United States Patent
Kang et al.

(10) Patent No.: US 11,542,171 B2
(45) Date of Patent: Jan. 3, 2023

(54) METHOD FOR PREPARING ZSM-5 ZEOLITE

(71) Applicant: KOREA RESEARCH INSTITUTE OF CHEMICAL TECHNOLOGY, Daejeon (KR)

(72) Inventors: Na Young Kang, Daejeon (KR); Yong Ki Park, Daejeon (KR); Chang Hwan Kim, Daejeon (KR); Yu Jin Lee, Dangjin-si (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 61 days.

(21) Appl. No.: 17/058,208

(22) PCT Filed: May 2, 2019

(86) PCT No.: PCT/KR2019/005992
§ 371 (c)(1),
(2) Date: Nov. 24, 2020

(87) PCT Pub. No.: WO2019/235754
PCT Pub. Date: Dec. 12, 2019

(65) Prior Publication Data
US 2021/0155489 A1 May 27, 2021

(30) Foreign Application Priority Data
Jun. 8, 2018 (KR) .................. 10-2018-0065795

(51) Int. Cl.
| | | |
|---|---|---|
| *C01B 39/38* | (2006.01) | |
| *B01J 29/40* | (2006.01) | |
| *C01B 33/26* | (2006.01) | |
| *C07C 2/86* | (2006.01) | |
| *B01J 37/03* | (2006.01) | |
| *B01J 37/08* | (2006.01) | |
| *B01J 35/00* | (2006.01) | |

(52) U.S. Cl.
CPC .............. *C01B 39/38* (2013.01); *B01J 29/40* (2013.01); *B01J 35/002* (2013.01); *B01J 37/036* (2013.01); *B01J 37/08* (2013.01); *C01B 33/2807* (2013.01); *C07C 2/864* (2013.01); *B01J 2219/00033* (2013.01); *B01J 2219/00051* (2013.01); *B01J 2219/00168* (2013.01); *B01J 2219/00747* (2013.01); *B01J 2229/34* (2013.01); *C01P 2002/72* (2013.01); *C01P 2004/03* (2013.01); *C01P 2004/30* (2013.01); *C07C 2529/40* (2013.01); *Y02P 20/52* (2015.11); *Y02P 30/40* (2015.11)

(58) Field of Classification Search
CPC . B01J 29/40; B01J 37/036; B01J 37/08; B01J 35/002; B01J 2219/00168; B01J 2219/00051; B01J 2219/00033; B01J 2219/00747; C01P 2002/72; C01P 2002/70; C01P 2004/03; C01P 2004/30; Y02P 20/52; Y02P 30/40; C01B 33/2807; C01B 39/38; C07C 2529/40; C07C 1/20; C07C 11/04; C07C 11/06; C10G 11/05; C10G 2400/20
USPC ........... 502/77; 423/709, 710, 713; 208/106; 585/520, 638, 639
See application file for complete search history.

(56) References Cited

U.S. PATENT DOCUMENTS

| | | | |
|---|---|---|---|
| 7,842,277 B2 * | 11/2010 | Roth ...................... | B01J 29/047 585/407 |
| 9,539,545 B2 * | 1/2017 | Elomari ............... | B01D 53/228 |
| 2014/0024523 A1 * | 1/2014 | Lai ........................ | B01J 37/0045 423/700 |
| 2014/0056805 A1 * | 2/2014 | Kim ....................... | C01B 39/38 423/709 |
| 2015/0099912 A1 | 4/2015 | Nesterenko et al. | |

FOREIGN PATENT DOCUMENTS

| | | |
|---|---|---|
| EP | 0 025 799 A1 | 4/1981 |
| EP | 0 253 449 B1 | 10/1991 |
| JP | S63-25214 A | 2/1988 |
| JP | 2013-508253 A | 3/2013 |
| KR | 90-001487 B1 | 3/1990 |
| KR | 10-2005-0115693 A | 12/2005 |
| KR | 10-2011-0042740 A | 4/2011 |
| KR | 10-2014-0033542 A | 3/2014 |

(Continued)

OTHER PUBLICATIONS

Kokotailo et al., "Structure of synthetic zeolite ZSM-5", Nature, vol. 272, Mar. 1978.*

(Continued)

*Primary Examiner* — Elizabeth D Wood
(74) *Attorney, Agent, or Firm* — Hauptman Ham, LLP (57) ABSTRACT

The present invention relates to a method for preparing ZSM-5 zeolite. The present invention can provide a method for preparing ZSM-5 zeolite comprising the steps of: preparing a first solution in a solution state by heating a mixture comprising a silica source, an alumina source, a neutralizing agent and a crystalline ZSM-5 nucleus; preparing a reaction mother liquid by mixing a second solution comprising salts into the first solution; and continuously crystallizing by continuously supplying the reaction mother liquid to a hydrothermal synthesis reactor, wherein formula [1] below is satisfied.

$0.20 \leq W_a/W_b \leq 0.40$  Formula [1]

8 Claims, 6 Drawing Sheets

(56) References Cited

FOREIGN PATENT DOCUMENTS

KR      10-2016-0027346  A      3/2016
WO             80/02026  A1    10/1980
WO          2011/049333  A2     4/2011

OTHER PUBLICATIONS

Jia et al. "Recycling Mother Liquor to Synthesize Mesoporous SBA Silica", Asian Journal of Chemistry, vol. 25, No. 17, (2013), pp. 9627-9631.*
Britton et al., "The Assembly and Use of Continuous-Flow Systems for Chemical Synthesis", Nature Protocols, vol. 12, No. 11, (2017), pp. 2423-2446.*
Continuous flow synthesis of ZSM-5 zeolite on the order of seconds, PNAS vol. 113, No. 50, (20160, pp. 14267-14271.*
International Search Report dated Aug. 22, 2019, in connection with corresponding International Patent Application No. PCT/KR2019/005992.
Office Action dated Feb. 14, 2022, for Japanese Patent Application No. 2020-565839, along with an English machine translation.
Extended European Search Report dated Nov. 17, 2021, for corresponding European Patent Application No. 19815590.5.
Office Action dated Aug. 11, 2022 for Saudi Arabia Patent Application No. 520420581, along with an English translation.

* cited by examiner

METHOD FOR PREPARING ZSM-5 ZEOLITE

CROSS REFERENCE TO RELATED APPLICATION

This present application is a national stage filing under 35 U.S.C § 371 of PCT application number PCT/KR2019/005992 filed on May 02, 2019 which is based upon and claims the benefit of priority to Korean Patent Application No. 10-2018-0065795 filed on Jun. 08, 2018 in the Korean Intellectual Property Office. The disclosures of the above-listed applications are hereby incorporated by reference herein in their entireties.

TECHNICAL FIELD

The present invention relates to a method for preparing ZSM-5-based zeolite.

BACKGROUND ART

Zeolite has a tri-dimensional specific structure of alumino-silicate, and has larger micropores and better ion exchangeability than other alumino-silicate crystals, and thus, is widely used as a catalyst, an adsorbent, a molecular sieve, an ion exchanger, and the like.

A use of natural zeolite is limited due to the structural restriction thereof, but a use of synthetic zeolite is currently gradually being expanded. In order to diversify the use of zeolite, it is demanded that the crystal size, the particle size distribution, the shape, and the like of zeolite as well as the economical synthetic method thereof are optionally adjusted.

ZSM-5 zeolite forms three-dimensional pores composed of a 10-tetrahedron ring, and has a medium size between zeolite X and Y and zeolite Y. In addition, the ZSM-5 zeolite is a kind of pentasil zeolite which is a shape-selective catalyst representing specific adsorption and diffusion properties, and has a high SiO2/Al2O3 ratio to generally have good thermal stability, have hydrophobicity, and have a large Lewis acid site and a small Bronsted acid site.

A batch reactor was conventionally used in the preparation of ZSM-5 zeolite. That is, a method in which a raw material including a silica source and an alumina source and a reactant slurry including an aqueous alkaline solution are supplied to a batch reactor equipped with stirring blades and saturated steam are introduced to derive a zeolite-forming reaction by contact mixing under pressurization and heating conditions, was used.

However, in the preparation method using a batch reactor, it is impossible to implement the next process before completing a zeolite-forming reaction of a reactant slurry. Therefore, an output is determined by a volume of the batch reactor and overall productivity is deteriorated.

Thus, in order to overcome limitation of the preparation method using the conventional batch reactor, development of a method for preparing ZSM-5 zeolite by continuous synthesis, is demanded.

DISCLOSURE

Technical Problem

An object of the present invention is to provide a method for preparing ZSM-5-based zeolite, which may be prepared by continuous synthesis.

Technical Solution

In one general aspect, a method for preparing ZSM-5-based zeolite includes: heating a mixture including a silica source, an alumina source, a neutralizing agent, and a crystalline ZSM-5 nucleus to prepare a first solution in a solution state; mixing a second solution including a salt with the first solution to prepare a reaction mother liquor; and continuously supplying the reaction mother liquor to a hydrothermal synthesis reactor to perform continuous crystallization, wherein the following equation is satisfied:

$$0.20 \leq W_a/W_b \leq 0.40 \quad \text{[Equation 1]}$$

wherein $W_a$ is a content of the salt in the reaction mother liquor, and $W_b$ is a content of silica in the reaction mother liquor.

A heating temperature may be 30 to 60° C. and a heating time may be 1 to 3 hours in the step of preparing the first solution.

The salt may include sodium sulfate ($Na_2SO_4$), sodium nitrate ($NaNO_3$), trisodium phosphate ($Na_3PO_4$), or a combination thereof.

The hydrothermal synthesis reactor may be a continuous stirred-tank reactor (CSTR) or a plug flow reactor (PFR).

The second solution may be an unreacted remaining solution of the hydrothermal synthesis reactor.

In the step of preparing the reaction mother liquor, the second solution may be recirculated to a front end of the hydrothermal synthesis reactor and mixed with the first solution.

A reaction temperature of the step of continuous crystallization may be 150 to 200° C.

The reaction mother liquor may have a viscosity of 1000 to 2700 cP.

Equation 1 may satisfy the following Equation 2:

$$0.22 \leq W_a/W_b \leq 0.32 \quad \text{[Equation 2]}$$

wherein $W_a$ is a content of the salt in the reaction mother liquor, and $W_b$ is a content of silica in the reaction mother liquor.

In another general aspect, ZSM-5-based zeolite prepared from the method for preparing ZSM-5-based zeolite of the embodiment of the present invention is provided.

In still another general aspect, a method for preparing a light olefin from a hydrocarbon, an oxygen-containing organic compound, or a mixture thereof, using the ZSM-5-based zeolite of the embodiment of the present invention, is provided.

Advantageous Effects

According to the method for preparing ZSM-5-based zeolite of an embodiment of the present invention, reactor clogging which may occur due to gelation of the reaction mother liquor is prevented, thereby preparing ZSM-5-based zeolite by continuous synthesis for a long period of time.

In addition, according to the method for preparing ZSM-5-based zeolite of an embodiment of the present invention, single phase ZSM-5-based zeolite having high crystallinity of a uniform size may be easily continuously prepared within a short time.

Thus, according to the method for preparing ZSM-5-based zeolite of an embodiment of the present invention, productivity of zeolite is maximized, and thus, process economic feasibility is improved and industrial applicability of ZSM-5-based zeolite catalyst production technique is expected.

BEST MODE

Unless otherwise defined herein, all terms used in the specification (including technical and scientific terms) may have the meaning that is commonly understood by those skilled in the art. Throughout the present specification, unless explicitly described to the contrary, "comprising" any elements will be understood to imply further inclusion of other elements rather than the exclusion of any other elements. In addition, unless explicitly described to the contrary, a singular form includes a plural form herein.

Unless otherwise defined throughout the present specification, "A to B" refers to "A or more and B or less".

In one general aspect, a method for preparing ZSM-5-based zeolite includes: heating a mixture including a silica source, an alumina source, a neutralizing agent, and a crystalline ZSM-5 nucleus to prepare a first solution in a solution state; mixing a second solution including a salt with the first solution to prepare a reaction mother liquor; and continuously supplying the reaction mother liquor to a hydrothermal synthesis reactor to perform continuous crystallization, wherein the following equation is satisfied:

$$0.20 \leq W_a/W_b \leq 0.40 \quad \text{[Equation 1]}$$

wherein $W_a$ is a content of the salt in the reaction mother liquor, and $W_b$ is a content of silica in the reaction mother liquor.

For preparing ZSM-5-based zeolite by a continuous reaction, a process in which a reaction mother liquor for continuous zeolite synthesis is supplied, and simultaneously, zeolite cakes crystallized by a high-temperature hydrothermal synthesis reactor are continuously recovered, should continuously proceed.

As an example, when water glass which is cheapest and most commonly used is used as a silica source for preparing ZSM-5-based zeolite, a rapid acid-base reaction occurs due to an acid component which is added for removing an excess amount of a base component in the water glass, and subsequently, a viscosity of a mixture is rapidly increased, thereby forming a hardened gel.

In the case of synthesis using a batch reactor as in the conventional art, there is no process of filling the gel in a hardened form and then further filling the gel before synthesis is completed, and thus, no problem in operation is found; however, in the case of continuous synthesis, continuous injection of a hardened gel into the high-temperature hydrothermal reactor using a high-pressure injection pump is impossible, and thus, a synthetic mother liquor in the form of a low-viscosity solution should be prepared. At the same time, clogging in the reaction should be prevented so that continuous synthesis proceeds for a long period of time.

An embodiment of the present invention provides a method for preparing single phase ZSM-5-based zeolite having high crystallinity of a uniform size easily and continuously within a short time, by solving the above problem.

Specifically, the single phase ZSM-5-based zeolite having high crystallinity of a uniform size may be prepared by continuous synthesis, by using a mixture in which a first solution obtained in a solution state by heating a mixture including a silica source, an alumina source, a neutralizing agent, and a crystalline ZSM-5 nucleus and a second solution including a salt are mixed as a reaction mother liquor.

The mixture including a silica source, an alumina source, a neutralizing agent, and a crystalline ZSM-5 nucleus gels at room temperature by an acid-base reaction of the silica source and the neutralizing agent, and when the mixture is used as it is as the reaction mother liquor, it is difficult to continuously inject the hardened gel to a reactor.

Thus, the mixture including a silica source, an alumina source, a neutralizing agent, and a crystalline ZSM-5 nucleus is heated to be in a solution state having a low viscosity, thereby allowing continuous injection. In the solution state, water may be used as a solvent, and a low-viscosity aqueous solution may be prepared after heating and used.

More specifically, a heating temperature for preparing the mixture including a silica source, an alumina source, a neutralizing agent, and a crystalline ZSM-5 nucleus in an aqueous solution state may be 30 to 60° C. In addition, a heating time may be 1 to 3 hours.

Under the heating condition as described above, the first solution in an aqueous solution state is easily prepared without a problem that the mixture including a silica source, an alumina source, a neutralizing agent, and a crystalline ZSM-5 nucleus is formed into a gel in a non-uniform state, and when the mixture is mixed with the second solution including a salt in a post-process, it is difficult to obtain an aqueous solution in a uniform state due to difficult mixing, and a problem that excessive energy is supplied to produce an aluminosilicate lump in which particles are agglomerated, and used in the continuous synthesis, which may be thus preferred.

In addition, the first solution does not include an organic structure-inducing material, and the silica source may be silica sol, water glass, or sodium silicate, and more specifically water glass.

The alumina source may be sodium aluminate, aluminum nitrate, aluminum sulfate, aluminum chloride, and a combination thereof, and preferably sodium aluminate, aluminum nitrate, aluminum sulfate, and a combination thereof.

The neutralizing agent is a material added for alleviating a difficulty in reactant composition control due to the silica source and the alumina source which contain a large amount of alkali components, and may be a nitric acid, a sulfuric acid, or aluminum sulfate, and specifically a sulfuric acid.

In the method for preparing ZSM-5-based zeolite of an embodiment of the present invention, a final reaction mother liquor is prepared by mixing the second solution including a salt with the first solution to prepare the reaction mother liquor, in which the first solution and the second solution may be mixed so that the reaction mother liquor satisfies the following Equation 1:

$$0.20 \leq W_a/W_b \leq 0.40 \quad \text{[Equation 1]}$$

wherein $W_a$ is a content of the salt in the reaction mother liquor, and $W_b$ is a content of silica in the reaction mother liquor.

Equation 1 may, more specifically, satisfy the following Equation 2:

$$0.22 \leq W_a/W_b \leq 0.32 \quad \text{[Equation 2]}$$

When a ratio of the content of the salt to the content of silica in the final reaction mother liquor is too low, a viscosity of the final reaction mother liquor is rapidly increased to make continuous injection into the hydrothermal synthesis reactor impossible, and when the ratio is too high, continuous injection is possible, but zeolite in another crystalline phase grows together or the crystallinity of ZSM-5 is lowered after performing a short continuous reaction, so that it is difficult to prepare single crystalline and high crystalline ZSM-5 by performing a continuous reaction for a long period of time.

As a solvent of the second solution, water may be used also.

In addition, when the contents of the salt and the silica in the second solution satisfy the above relation, a phenomenon in which zeolite is deposited and grows in the reactor is suppressed to prevent clogging in the reaction, and thus, it is possible to prepare single phase ZSM-5-based zeolite having high crystallinity of a uniform size, which is confirmed in the Examples described later.

In the second solution including a salt, the salt may include sodium sulfate ($Na_2SO_4$), sodium nitrate ($NaNO_3$), trisodium phosphate ($Na_3PO_4$), or a combination thereof, and preferably may include sodium sulfate.

In the second solution including a salt, the salt may be included at 1 to 5 wt % with respect to a total amount of the reaction mother liquor, but is not necessarily limited thereto.

In the method for preparing ZSM-5-based zeolite of an embodiment of the present invention, the reaction mother liquor may have a low viscosity in a range of 1000 to 2700 cp, and thus, may be stirred without intervention of large shear force and continuously introduced to the reactor to allow continuous synthesis.

In the method for preparing ZSM-5-based zeolite of an embodiment of the present invention, the step of continuously supplying the reaction mother liquor to the hydrothermal synthesis reactor to perform continuous crystallization may be performed at a temperature of 150 to 200° C.

In addition, a residence time in the hydrothermal synthesis reactor of the reaction mother liquor may be 6 hours to 300 hours, but is not particularly limited thereto.

In addition, the hydrothermal synthesis reactor may be a continuous stirred-tank reactor (CSTR) or a plug flow reactor (PFR).

In the method for preparing ZSM-5-based zeolite of an embodiment of the present invention, an embodiment of preparation of the reaction mother liquor and introduction thereof to the reactor will be described in detail. The reaction mother liquor may be continuously introduced to the reactor by preparing the first solution and the second solution separately and then mixing the solutions before introduction to the reactor.

In another embodiment, by using a remaining solution after a hydrothermal synthesis reaction, a part of the unreacted remaining solution in the hydrothermal synthesis reactor may be recirculated to a front end of the hydrothermal synthesis reactor and the first solution and the remaining solution may be mixed and introduced to the reactor.

The unreacted remaining solution in the hydrothermal synthesis reactor may include the salt described above and the remaining solution is recirculated to a front end of the reactor and mixed with the first solution to prepare the reaction mother liquor which is continuously introduced into the reactor, thereby allowing operation of the process without separate preparation of the second solution.

Thus, it becomes possible to simplify the process and the embodiment may be more preferred.

The method for preparing ZSM-5-based zeolite of an embodiment of the present invention may further include: continuously supplying the reaction mother liquor to the hydrothermal synthesis reactor to perform continuous crystallization; then filtering and washing crystallized ZSM-5; and drying the ZSM-5 at a temperature of 120° C. for 10 hours to 15 hours.

Thus, single phase ZSM-5-based zeolite having high crystallinity of a uniform size may be finally obtained.

The ZSM-5-based zeolite prepared in the preparation method of an embodiment of the present invention may be used as a catalyst for preparing a light olefin from a hydrocarbon, an oxygen-containing organic compound, or a mixture thereof.

Here, the ZSM-5-based zeolite may be used as it is, or as a catalyst after specific treatment such as surface modification, and a specific embodiment is not particularly limited in the present invention.

In addition, the hydrocarbon may include commonly available naphtha, and the oxygen-containing organic compound may include methanol, but these are not particularly limited in the present invention.

In addition, the light olefin may include ethylene and/or propylene, but is not limited thereto.

Hereinafter, the preferred Examples and Comparative Examples of the present invention will be described. However, the following Examples are only a preferred example, and the present invention is not limited thereto.

Example 1

(Step 1) To a solution obtained by adding 23 kg of distilled water to 29 kg of water glass ($SiO_2$=20 wt %, $Na_2O$=6 wt %) as a silica source, stirring the solution for 30 minutes, and then adding 0.4 kg of a crystalline ZSM-5 nucleus, a solution in which 3.1 kg of an aluminum salt ($Al_2O_3$=8 wt %), 0.9 kg of a sulfuric acid, and 23 kg of distilled water were mixed by stirring for 30 minutes was added, and the mixture was maintained for 1 hour to prepare a first solution. Here, for preventing gelation of the first solution, the first solution was heated to 60° C. to be prepared in an aqueous solution state.

(Step 2) To 40 kg of the first solution prepared in Step 1, 60 kg of a second solution containing a salt ($Na_2SO_4$=2 wt %, $Na_2O$=2 wt %, $SiO_2$=4 wt %) was added, the solution was stirred for 1 hour, and then aged for one day to prepare a reaction mother liquor. Results of viscosity analysis of the reaction mother liquor prepared as described above are shown in Table 1.

A viscosity of the reaction mother liquor was measured at 25° C. using a viscometer (BROOKFIELD DV-II+Pro).

Figure 1:
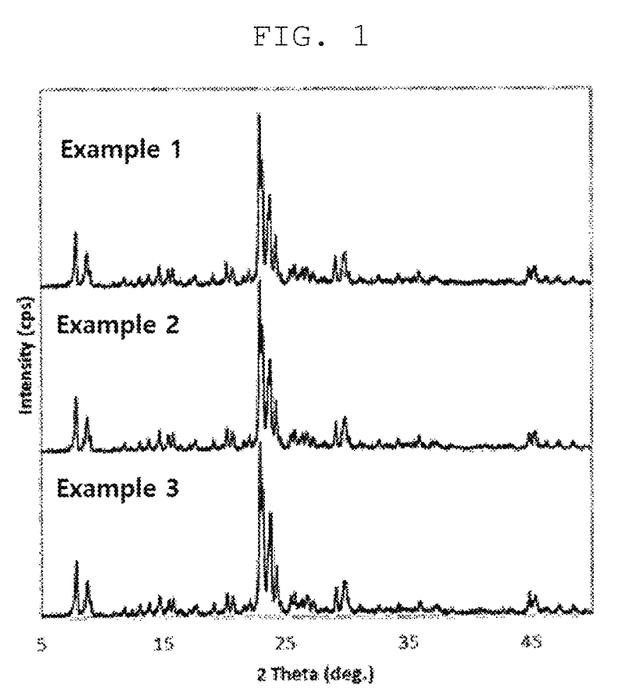
FIG. 1 is X-ray diffraction analysis data of ZSM-5 prepared in Examples 1 to 3.
Figure 2:
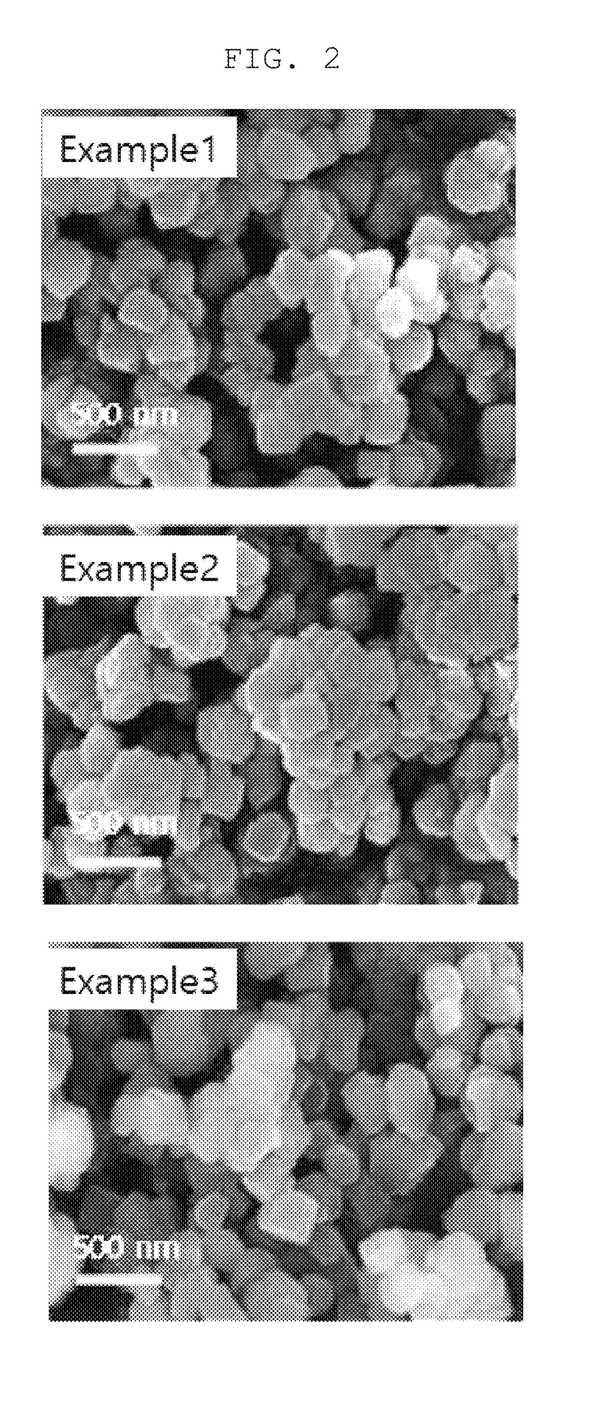
FIG. 2 is scanning electron microscope (SEM) photographs of ZSM-5 prepared in Examples 1 to 3.

(Step 3) The reaction mother liquor prepared in Step 2 was injected at a speed of 20 g/min to an autoclave reactor heated to 150° C., thereby performing crystallization. While the hydrothermal synthesis reaction proceeded, the reaction mother liquor was continuously supplied to prolong a crystallization reaction for 30 days or more, the crystal structure and the shape of zeolite obtained after continuous synthesis were analyzed by XRD (Rigaku Model D/Max III) and a scanning electron microscope, and the results are shown in Table 1, FIG. 1, and FIG. 2.

The crystal structure and the crystallinity of the obtained zeolite were analyzed by collecting 2θ 7-9° and 22-25° data corresponding to a specific peak of ZSM-5 using an X-ray diffraction analyzer (Rigaku Model D/Max III), and the crystallinity was calculated as follows. (ACZeo-ZN030 (SiO$_2$/Al$_2$O$_3$ mole ratio=30) available from Albemarle was used as commercial ZSM-5.)

$$\text{Crystallinity (\%)} = \frac{\text{Peak area at 22-25° obtained after X-ray diffraction analysis of synthesized product}}{\text{Peak area at 22-25° obtained after X-ray diffraction analysis of commercial ZSM-5}} \times 100$$

Figure 5:
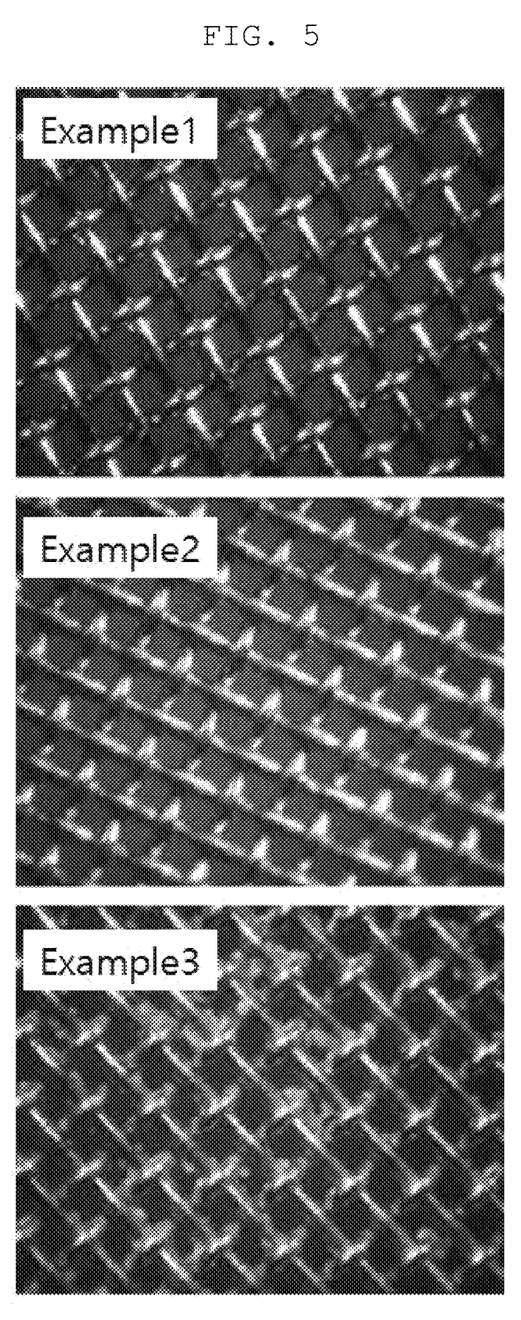
FIG. 5 is photographs of mesh attached to a continuous synthesis reactor, observed by an optical microscope, after preparing ZSM-5 of Examples 1 to 3.

In addition, for confirming clogging in the reactor, a mesh having a 45 μm-sized sieve opening attached to the inside of the reactor was observed by an optical microscope and the results are shown in FIG. 5.

Example 2

Zeolite was prepared in the same manner as in Example 1, except that 50 kg of the second solution was added to 50 kg of the first solution in Step 2 of Example 1.

Results of viscosity analysis of the reaction mother liquor are shown in Table 1. The crystal structure and the shape of zeolite obtained after continuous synthesis were analyzed by XRD and SEM, and the results are shown in Table 1, FIG. 1, and FIG. 2.

In addition, a mesh having a 45 μm-sized sieve opening attached to the inside of the reactor was analyzed by an optical microscope and the results are shown in FIG. 5.

Example 3

Zeolite was prepared in the same manner as in Example 1, except that 40 kg of the second solution was added to 60 kg of the first solution in Step 2 of Example 1.

Results of viscosity analysis of the first continuous synthesis mother liquor are shown in Table 1. The crystal structure and the shape of zeolite obtained after continuous synthesis were analyzed by XRD and SEM, and the results are shown in Table 1, FIG. 1, and FIG. 2.

A mesh having a 45 μm-sized sieve opening attached to the inside of the reactor was analyzed by an optical microscope and the results are shown in FIG. 5.

Comparative Example 1

Zeolite was prepared in the same manner as in Example 1, except that 95 kg of the second solution was added to 5 kg of the first solution in Step 2 of Example 1.

Results of viscosity analysis of the reaction mother liquor are shown in Table 1.

A continuous synthesis period was maintained for 3 days, and then continuous injection and recovery were impossible due to clogging.

Figure 3:
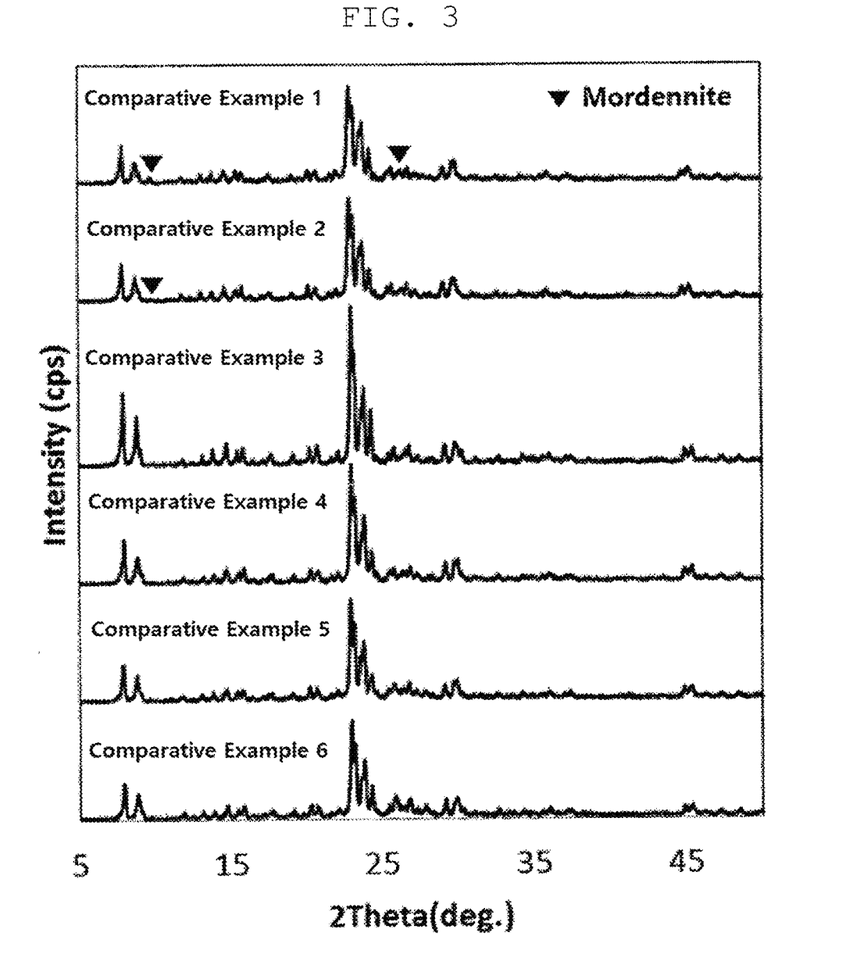
FIG. 3 is X-ray diffraction analysis data of ZSM-5 prepared in Comparative Examples 1 to 6.
Figure 4:
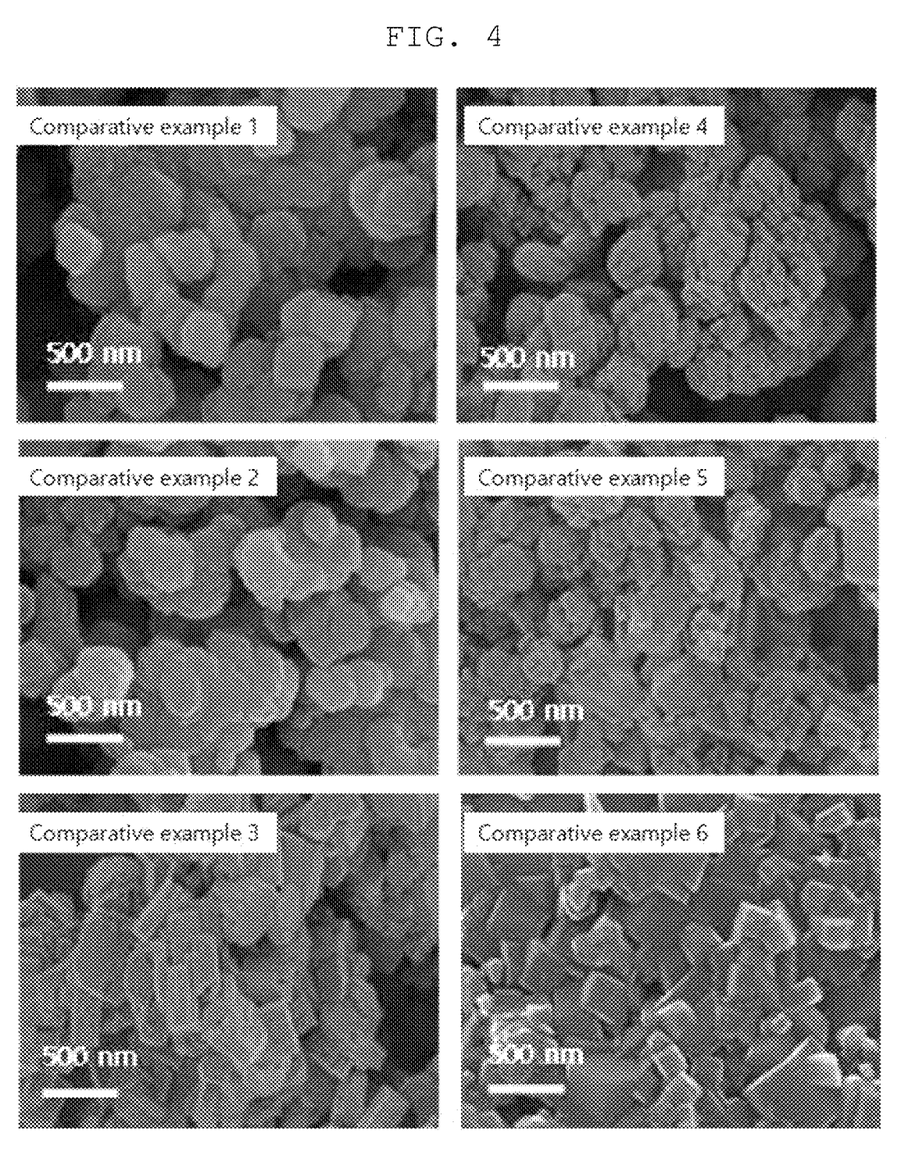
FIG. 4 is scanning electron microscope (SEM) photographs of ZSM-5 prepared in Comparative Example 1 to 6.

The crystal structure and the shape of zeolite obtained after continuous synthesis were analyzed by XRD and SEM, and the results are shown in Table 1, FIG. 3, and FIG. 4.

Figure 6:
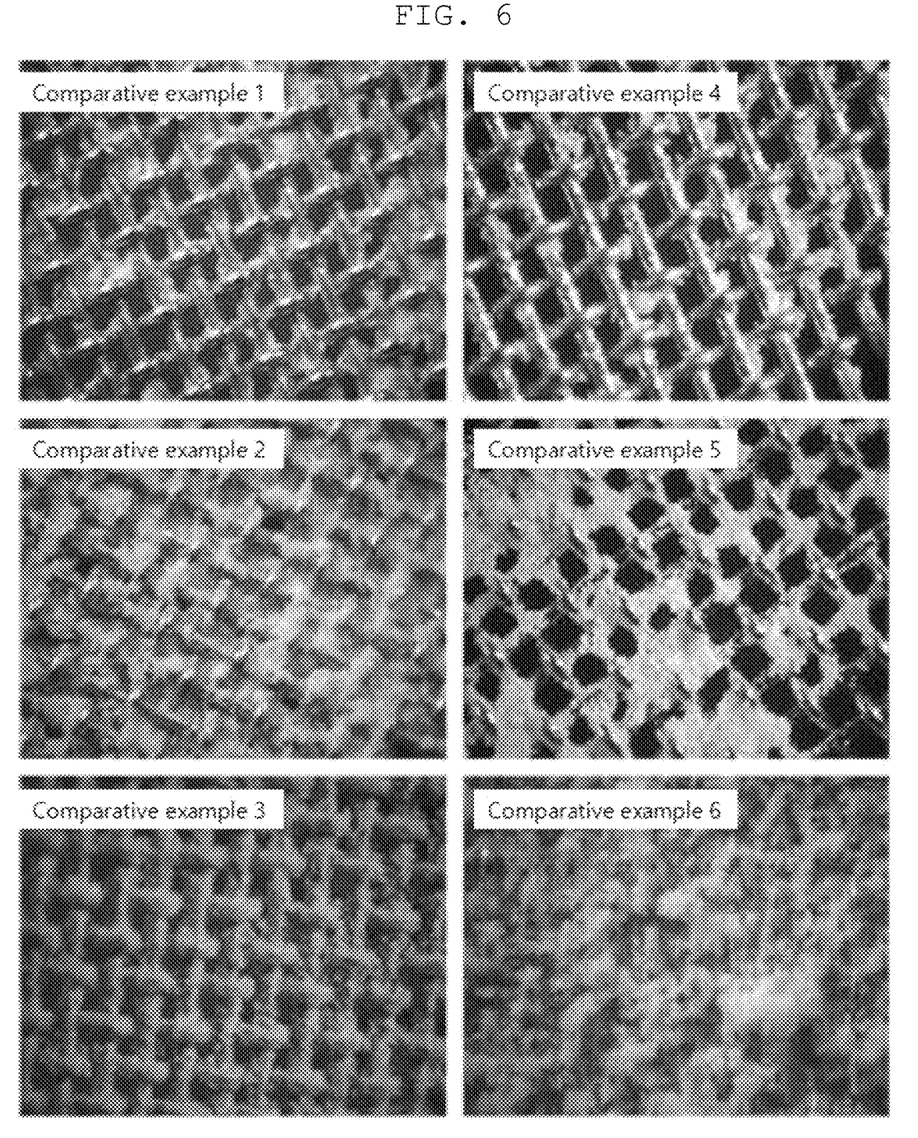
FIG. 6 is photographs of mesh attached to a continuous synthesis reactor, observed by an optical microscope, after preparing ZSM-5 of Comparative Examples 1 to 6.

A mesh having a 45 μm-sized sieve opening attached to the inside of the reactor was analyzed by an optical microscope and the results are shown in FIG. 6.

Comparative Example 2

Zeolite was prepared in the same manner as in Example 1, except that 90 kg of the second solution was added to 10 kg of the first solution in Step 2 of Example 1.

Results of viscosity analysis of the reaction mother liquor are shown in Table 1.

A continuous synthesis period was maintained for 5 days, and then continuous injection and recovery were impossible due to clogging.

The crystal structure and the shape of a molecular sieve obtained after continuous synthesis were analyzed by XRD and SEM, and the results are shown in Table 1, FIG. 3, and FIG. 4.

A mesh having a 45 μm-sized sieve opening attached to the inside of the reactor was analyzed by an optical microscope and the results are shown in FIG. 6.

Comparative Example 3

Zeolite was prepared in the same manner as in Example 1, except that 80 kg of the second solution was added to 20 kg of the first solution in Step 2 of Example 1.

Results of viscosity analysis of the reaction mother liquor are shown in Table 1.

A continuous synthesis period was maintained for 8 days, and then continuous injection and recovery were impossible due to clogging.

The crystal structure and the shape of zeolite obtained after continuous synthesis were analyzed by XRD and SEM, and the results are shown in Table 1, FIG. 3, and FIG. 4.

A mesh having a 45 μm-sized sieve opening attached to the inside of the reactor was analyzed by an optical microscope and the results are shown in FIG. 6.

Comparative Example 4

Zeolite was prepared in the same manner as in Example 1, except that 30 kg of the second solution was added to 70 kg of the first solution in Step 2 of Example 1.

Results of viscosity analysis of the reaction mother liquor are shown in Table 1.

A continuous synthesis period was maintained for about 12 hours, and then continuous injection and recovery were impossible due to clogging.

The crystal structure and the shape of zeolite obtained after continuous synthesis were analyzed by XRD and SEM, and the results are shown in Table 1, FIG. 3, and FIG. 4.

A mesh having a 45 μm-sized sieve opening attached to the inside of the reactor was analyzed by an optical microscope and the results are shown in FIG. 6.

Comparative Example 5

Zeolite was prepared in the same manner as in Example 1, except that 20 kg of the second solution was added to 80 kg of the first solution in Step 2 of Example 1.

Results of viscosity analysis of the reaction mother liquor are shown in Table 1.

A continuous synthesis period was maintained for about 8 hours, and then continuous injection and recovery were impossible due to clogging.

The crystal structure and the shape of zeolite obtained after continuous synthesis were analyzed by XRD and SEM, and the results are shown in Table 1, FIG. 3, and FIG. 4.

A mesh having a 45 μm-sized sieve opening attached to the inside of the reactor was analyzed by an optical microscope and the results are shown in FIG. 6.

Comparative Example 6

Zeolite was prepared in the same manner as in Example 1, except that 100 kg of the first solution was used without adding a remaining solution in Step 2 of Example 1.

Results of viscosity analysis of the reaction mother liquor are shown in Table 1.

A continuous synthesis period was maintained for about 2 hours, and then continuous injection and recovery were impossible due to clogging.

The crystal structure and the shape of zeolite obtained after continuous synthesis were analyzed by XRD and SEM, and the results are shown in Table 1, FIG. 3, and FIG. 4.

A mesh having a 45 μm-sized sieve opening attached to the inside of the reactor was analyzed by an optical microscope and the results are shown in FIG. 6.

when a $Na_2SO_4/SiO_2$ weight ratio in the final reaction mother liquor was high, a molecular sieve which grew partly with a mordenite phase having an undesired different crystal structure was obtained.

Besides, as seen from FIGS. 5 and 6, as a result of confirming a metal mesh attached to the inside of the continuous synthesis reactor, it was found that a degree of attaching and growing of zeolite varied depending on the content of the salt in the mother liquor, and in the Comparative Examples, a speed of attaching and growing of zeolite was severe as compared with the Examples, and a period during which continuous synthesis was possible became very short.

The invention claimed is:

1. A method for preparing ZSM-5-based zeolite, the method comprising:
   heating a mixture including a silica source, an alumina source, a neutralizing agent, and a crystalline ZSM-5 nucleus to prepare a first solution in a solution state;
   mixing a second solution including a salt with the first solution to prepare a reaction mother liquor; and

TABLE 1

| | Used amount of raw material (wt%) | | Content of salt in reaction mother liquor $(Na_2SO_4/SiO_2$ wt %) | Viscosity of reaction mother liquor (cp) | Continuous synthesis period (day) | Crystal phase/crystallinity (%) of molecular sieve after continuous synthesis |
|---|---|---|---|---|---|---|
| | First solution | Second solution | | | | |
| Comparative Example 1 | 5 | 95 | 0.51 | 200 | 3 | ZSM-5 + Mordenite/84 |
| Comparative Example 2 | 10 | 90 | 0.49 | 500 | 5 | ZSM-5 + Mordenite/91 |
| Comparative Example 3 | 20 | 80 | 0.43 | 700 | 8 | ZSM-5/99 |
| Example 1 | 40 | 60 | 0.32 | 1000 | >30 | ZSM-5/100 |
| Example 2 | 50 | 50 | 0.27 | 1500 | >30 | ZSM-5/100 |
| Example 3 | 60 | 40 | 0.22 | 2700 | >30 | ZSM-5/100 |
| Comparative Example 4 | 70 | 30 | 0.16 | 3500 | 0.50 | ZSM-5/95 |
| Comparative Example 5 | 80 | 20 | 0.11 | 6800 | 0.33 | ZSM-5/80 |
| Comparative Example 6 | 100 | 0 | 0 | 9000 | 0.08 | ZSM-5/77 |

As seen from the above Table 1, when the ZSM-5 molecular sieve was synthesized by a continuous synthesis reaction, the reaction mother liquor according to the present invention was used, thereby allowing continuous injection of the reaction mother liquor and continuous recovery of the ZSM-5 molecular sieve without clogging in the reactor, and synthesizing the ZSM-5 molecular sieve having good quality with a uniform particle size and high crystallinity of a single phase.

Upon confirmation of an effect depending on an added amount of the salt in the prepared reaction mother liquor, it was found that when a $Na_2SO_4/SiO_2$ weight ratio in the prepared final reaction mother liquor was in a range of 0.20 to 0.40, and more specifically 0.22 to 0.32, continuous synthesis for 30 days or more was possible, and a high crystalline ZSM-5 molecular sieve of a single phase was obtained. However, when a $Na_2SO_4/SiO_2$ weight ratio in the final reaction mother liquor was low, though a ZSM-5 molecular sieve of a single phase was obtained, a possible continuous synthesis period was very short by clogging, and continuously supplying the reaction mother liquor to a hydrothermal synthesis reactor to perform continuous crystallization,
wherein the following Equation 1 is satisfied:

$$0.2 \leq W_a/W_b \leq 0.40 \quad \text{[Equation 1]}$$

wherein $W_a$ is a content of the salt in the reaction mother liquor, and $W_b$ is a content of silica in the reaction mother liquor, and
wherein the reaction mother liquor has a viscosity of 1000 to 2700 cP.

2. The method for preparing ZSM-5-based zeolite of claim 1, wherein a heating temperature is 30 to 60° C. and a heating time is 1 to 3 hours in the preparing of a first solution.

3. The method for preparing ZSM-5-based zeolite of claim 1, wherein the salt includes sodium sulfate ($Na_2SO_4$), sodium nitrate ($NaNO_3$), trisodium phosphate ($Na_3PO_4$), or a combination thereof.

4. The method for preparing ZSM-5-based zeolite of claim 1, wherein the hydrothermal synthesis reactor is a continuous stirred-tank reactor (CSTR) or a plug flow reactor (PFR).

5. The method for preparing ZSM-5-based zeolite of claim 1, wherein the second solution is an unreacted remaining solution of the hydrothermal synthesis reactor.

6. The method for preparing ZSM-5-based zeolite of claim 5, wherein in the preparing of a reaction mother liquor, the second solution is recirculated to a front end of the hydrothermal synthesis reactor and mixed with the first solution.

7. The method for preparing ZSM-5-based zeolite of claim 1, wherein a reaction temperature in the performing of continuous crystallization is 150 to 200° C.

8. The method for preparing ZSM-5-based zeolite of claim 1, wherein Equation 1 satisfies the following Equation 2:

$$0.22 \leq W_a/W_b \leq 0.32 \qquad \text{[Equation 2]}$$

wherein $W_a$ is a content of the salt in the reaction mother liquor, and $W_b$ is a content of silica in the reaction mother liquor.

* * * * *